United States Patent
Sunshine et al.

(10) Patent No.: US 7,471,185 B2
(45) Date of Patent: *Dec. 30, 2008

(54) ALIGNED PARTICLE BASED SENSOR ELEMENTS

(75) Inventors: Steven A. Sunshine, Pasadena, CA (US); Beth C. Munoz, Pasadena, CA (US)

(73) Assignee: Smiths Detection, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/525,989

(22) Filed: Sep. 25, 2006

(65) Prior Publication Data

US 2007/0018779 A1    Jan. 25, 2007

Related U.S. Application Data (60) Division of application No. 09/600,346, filed as application No. PCT/US99/28282 on Nov. 30, 1999, now Pat. No. 7,113,069, which is a continuation of application No. 09/201,999, filed on Dec. 1, 1998, now abandoned.

(51) Int. Cl.
*H01C 7/00* (2006.01)
(52) U.S. Cl. ............ 338/34; 338/22 R; 338/225; 257/414
(58) Field of Classification Search ........... 338/22 R, 338/32 R, 34–35, 67, 224–225, 334; 257/414, 257/417, 426; 205/775, 787; 428/142–143, 428/221; 204/406, 415; 73/31.05
See application file for complete search history.

(56) References Cited

U.S. PATENT DOCUMENTS 2,636,962 A    4/1953    Bouyoucos (Continued)

FOREIGN PATENT DOCUMENTS

DE    19718584 C1    11/1998

(Continued)

OTHER PUBLICATIONS

Chen et al., "Novel vapor sensor based on chemical coupling effect of composite", SPIE vol. 3040, 1997, pp. 271-278.

*Primary Examiner*—Kyung Lee
(74) *Attorney, Agent, or Firm*—Foley & Lardner LLP (57) ABSTRACT

The present invention relates to a sensor array for detecting an analyte in a fluid, comprising first and second sensors formed by chemically sensitive resitors, wherein the first sensor comprises a region of aligned conductive material; or where each of the sensors comprises alternating regions of nonconductive regions and aligned conductive regions with each resistor providing an electrical path through both the nonconductive region and the aligned conductive region, while each sensor manifests a different electrical resistance during contact with sample fluids having different analyte concentrations via the monitoring arrangement of having the sensors electrically connected to an electrical measuring apparatus. The aligned conductive particle material is aligned by exposure to either of an electric, magnetic, optical, photo-electric, electromagnetic or mechanical field, which serves to improve signal to noise ratio of vapor sensors allowing Lower Detection Limits for vapors being sensed. Such Lower Detection Limits allow for identification of lower concentrations of hazardous material and is advantageous in medical applications, such as detection of disease states in a patient.

8 Claims, 4 Drawing Sheets

U.S. PATENT DOCUMENTS

| | | |
|---|---|---|
| 4,155,781 A | 5/1979 | Diepers |
| 4,198,851 A | 4/1980 | Janata |
| 4,245,506 A | 1/1981 | Meiklejohn |
| 4,433,320 A | 2/1984 | Murata et al. |
| 4,453,126 A | 6/1984 | Volgyesi |
| 4,581,204 A | 4/1986 | Voit |
| 4,644,101 A | 2/1987 | Jin et al. |
| 4,737,112 A | 4/1988 | Jin et al. |
| 4,838,347 A | 6/1989 | Dentini et al. |
| 4,923,739 A | 5/1990 | Jin et al. |
| 5,238,729 A * | 8/1993 | Debe .................... 428/142 |
| 5,512,882 A | 4/1996 | Stetter et al. |
| 5,571,401 A * | 11/1996 | Lewis et al. ............ 205/787 |
| 5,698,089 A | 12/1997 | Lewis et al. |
| 5,742,223 A | 4/1998 | Simendinger, III et al. |
| 5,942,674 A | 8/1999 | Logothetis et al. |
| 6,060,327 A | 5/2000 | Keen |
| 6,194,769 B1 * | 2/2001 | Martin et al. ............ 257/414 |
| 6,290,868 B1 | 9/2001 | Martin et al. |
| 7,113,069 B1 * | 9/2006 | Sunshine et al. ............ 338/34 |
| 2002/0142477 A1 * | 10/2002 | Lewis et al. ............ 436/151 |
| 2002/0149466 A1 | 10/2002 | Sunshine et al. |

FOREIGN PATENT DOCUMENTS

| | | |
|---|---|---|
| EP | 0306183 A2 | 3/1989 |
| EP | 0306183 A3 | 3/1989 |
| WO | WO 97/23777 | 7/1997 |
| WO | WO 99/00663 | 1/1999 |
| WO | WO 00/33062 | 6/2000 |

* cited by examiner

ALIGNED PARTICLE BASED SENSOR ELEMENTS

CROSS-REFERENCE TO RELATED PATENT APPLICATIONS

This application is a divisional application of U.S. patent application Ser. No. 09/600,346, filed Nov. 9, 2000, now U.S. Pat. No. 7,113,069, which is a National Stage application of PCT/US99/028282, filed Nov. 30, 1999, which is a continuation of U.S. patent application Ser. No. 09/201,999, filed Dec. 1, 1998, the disclosures of the non-abandoned applications are hereby incorporated by reference in their entirety for all purposes.

BACKGROUND OF THE INVENTION

Electronic noses are artificial sensory systems that are able to mimic chemical sensing. In some instances, electronic noses are arrays of sensors, which are able to generate electrical signals in response to analytes or vapors. For instance, it is possible to detect volatile materials by directly or indirectly measuring a response, such as a resistance, across each of the sensors in the array. Moreover, by providing different variables in each sensor of the array, such as the polymeric make-up of the sensors, it is possible to characterize various chemical materials according to the response of the array to that volatile material.

The potential applications of electronic noses are great. Examples of applications include, but are not limited to, environmental control, quality control, assessment of food and beverage products. For example, in relation to fish freshness, long chain carbonyl compounds, such as myristaldehyde, can be correlated with fresh fish, whereas short chain alcohols, dimethylsulfide and amines, which increase as a function of time, are characteristic of foul smelling fish.

U.S. Pat. No. 5,571,401, which issued to Lewis et al. (incorporated herein by reference), discloses sensor arrays useful for the detection of analytes. Each of these sensors comprise a resistor having a plurality of alternating nonconductive regions and conductive regions. As explained therein, gaps exist between the conductive regions and the nonconductive regions. In these sensors, the electrical path length and resistance of a given gap are not constant, but change as the nonconductive region absorbs, adsorbs or imbibes an analyte. The dynamic aggregate resistance provided by these gaps is, in part, a function of analyte permeation of the nonconductive regions.

The foregoing sensor is based on a conductive network in a nonconductive-matrix. The swelling of the nonconductive matrix causes the conductive region to move apart changing the resistance of the sensor. The change in the resistance of the sensor can be correlated to the concentration of the vapor to be detected. The greater the resistance change for a given level of vapor, the lower the detection limit of the vapor being identified. It is thus advantageous to maximize the resistance change associated with the sensor elements.

One of the major challenges in sensor technology today is to enhance the signal-to-noise ratio (S/N) of a sensor element. By increasing the S/N of a sensor element, a lower detection limit is possible (i.e., the lower the concentration of analyte it is possible to detect). This is particularly useful in applications such as the detection of low concentrations of explosives, landmine detection or in medical applications such as in the detection of microorganism off-gases.

The response of the sensors upon exposure to vapor is dependent on various factors. One such factor is the percentage of connected paths that are broken. The number of connected paths prior to exposure to a vapor is related to the percolation threshold. The percolation threshold is defined as the particle volume fraction at which the conductivity of the resistor increases rapidly (i.e., an infinite number of conductive paths are formed and the lattice essentially transforms from an insulator to a conductor). At low volume loadings, there are few connected paths; whereas at high volume loadings there are many connected paths. However, at low volume loadings, there is greater sensor resistance. Unfortunately, there is concomitantly a high degree of noise at low volume loadings so that the signal to noise ratio is unsatisfactorily low.

In view of the foregoing, there is a need in the art to improve the signal to noise of vapor sensors while maintaining low volume loading. Low volume loading sensors result in more resistance and thereby a broader detection limit and greater dynamic range. The current invention fulfills this and other needs.

SUMMARY OF THE INVENTION

In certain aspects, the present invention provides a sensor array for detecting an analyte in a fluid, comprising: first and second sensors wherein the first sensor comprises a region of aligned conductive material; and wherein the sensor array is electrically connected to an electrical measuring apparatus. Preferably, the first and second sensors are first and second chemically sensitive resistors, each of the chemically sensitive resistors comprising: a plurality of alternating regions comprising a nonconductive region, such as an organic material, and an aligned conductive region. The aligned conductive region comprises an aligned conductive material compositionally different from the nonconductive region. Moreover, each sensor, such as a resistor, provides an electrical path through the nonconductive region and the aligned conductive region; and a first response such as an electrical resistance, when contacted with a first fluid comprising an analyte at a first concentration, and a second response when contacted with a second fluid comprising the analyte at a second different concentration.

In certain embodiments, the conductive region can be aligned using various processing techniques including, but are not limited to, exposure to an electric field, a thermal field, a magnetic field, an electromagnetic field, a photoelectric field, a light field, a mechanical field or combinations thereof.

Various materials can form the aligned conductive region of the present invention. Such materials include, but are not limited to, conductive materials, semi-conductive materials, magnetic materials, photoresponsive materials and combinations thereof. The aligned conductive materials are preferably embedded in an organic matrix, such as a polymeric matrix.

In another aspect, the present invention relates to a system for detecting an analyte in a fluid, the system comprising: a sensor array comprising first and second sensors wherein the first sensor comprises a region of aligned conducting material. Preferably, the first and second sensors are first and second chemically sensitive resistors, each chemically sensitive resistor comprising a plurality of alternating regions comprising a nonconductive region and an aligned conductive region. Preferably, the aligned conductive region comprises an aligned conductive material compositionally different than the nonconductive region. Each sensor, such as a resistor, provides an electrical path through the nonconducting region and the aligned conductive region, a first response such as an electrical resistance, when contacted with a first fluid comprising an analyte at a first concentration and a second different response when contacted with a second fluid comprising the analyte at a second different concentration, wherein the difference between the first response and the second response of the first chemically sensitive resistor being different from the difference between the first response and the second response of the second chemically sensitive resistor under the same conditions; an electrical measuring device electrically connected to the sensor array; and a computer comprising a resident algorithm; wherein the electrical measuring device detecting the first and the second responses in each of the chemically sensitive resistors and the computer assembling the responses into a sensor array response profile.

In yet another aspect, the present invention relates to a method for detecting the presence of an analyte in a fluid that can be either a liquid or a gas. The method comprising: providing a sensor array comprising first and second sensors, wherein the first sensor comprises a region of aligned conductive material; and contacting the sensor array with the analyte to produce a response thereby detecting the presence of the analyte. Preferably, the first and second sensors are first and second chemically sensitive resistors, each comprising a plurality of alternating regions comprising a nonconductive region, such as an organic material, and an aligned conductive region. The aligned conductive region comprises an aligned conductive material compositionally different from the nonconductive region. In this method, each resistor provides an electrical path through the nonconducting region and the aligned conductive region, a first response such as an electrical resistance, when contacted with a first fluid comprising an analyte at a first concentration and a second different response when contacted with a second fluid comprising the analyte at a second different concentration.

These and other features and advantages of the invention will be more readily apparent and understood when read with the detailed description that follows.

DETAILED DESCRIPTION OF THE PREFERRED EMBODIMENTS

Improvement of the signal to noise ratio of vapor sensors allows for lower detection limits by increasing the dynamic range. Lower detection limits allow for the identification of lower concentration of materials. This is particularly useful when detecting hazardous materials or in various medical applications. Surprisingly, it has now been discovered that by intentionally aligning the conductive region, there is an increase in the detection limit, i.e., the sensor is capable of detecting lower concentrations of analyte. As such, the present invention provides a sensor array for detecting an analyte in a fluid, comprising: first and second sensors wherein the first sensor comprises a region of aligned conducting material; and wherein the sensor array is connected to an electrical measuring apparatus. Preferably, the first and second sensors are first and second chemically sensitive resistors, each of the chemically sensitive resistors comprising: a plurality of alternating regions comprising a nonconductive region, such as a nonconductive organic material, and aligned conductive region, such as an aligned conductive material or particle. The aligned conductive region is compositionally different from the nonconductive region. The sensors such as resistors, provide an electrical path through the alternating regions comprising a nonconductive region, such as an organic material, and an aligned conductive region, a first response when contacted with a first fluid comprising an analyte at a first concentration, and a second response when contacted with a second fluid comprising the analyte at a second different concentration.

As explained previously, the response upon exposure to a vapor is dependent on various factors. One such factor is the percentage of connected paths in the alternating regions that are broken. The number of connected paths prior to exposure to a vapor is related to the percolation threshold. The percolation threshold is defined as the volume fraction at which the conductivity of the resistor increases rapidly. At low volume loadings, there are very few connected paths. At high volume loadings, there are many connected paths. Upon exposure to vapors, composite sensors will exhibit a large change in resistance near their percolation threshold. Before the advent of the present invention, the noise level associated with such low volume loadings was prohibitively high. However, by aligning the conductive region, lower volume loadings can now be used. Moreover, by aligning the conductive region, the percolation threshold is easier to obtain at low volume loadings.

The sensors of the present invention have an aligned conductive region that results in reduced percolation thresholds. Reduced percolation thresholds mean that a slight swelling of the composite sensor can result is a very large change in resistance. This is because the few conductive particles are all participating in the connected paths, and any discontinuity in the connectivity results in a large resistance change. Thus, the alignment of the conductive region results in all of the particles participating in the connected electrical paths. By aligning the conductive region, these systems will produce a stable base resistance and thereby enhance the signal-to-noise ratio. To achieve equivalent or near equivalent noise levels, it is important to ensure that the alternating regions are stable. This can be accomplished in the present invention by, for example, cross-linking the polymer matrix in the nonconducting region or by any other suitable means.

The alignment of the conductive region, e.g., material or particles, is effected through the application of various processing techniques. For instance, polarization techniques can be used to align the conducting region. Suitable polarization techniques include, but are not limited to, exposure to an electric field, a thermal field, a magnetic field, an electromagnetic field, a photoelectric field, a light field, a mechanical field or combinations thereof. The techniques employed to align the particles depends in part on the particle composition.

Suitable particles for use in the present invention include particles with a permanent magnetic dipole including, but not limited to, iron, nickel or cobalt require the use of a magnetic field for polarization to occur. Particles such as carbon black, coke, $C_{60}$, and the like, $TiO_2$, $BaTiO_3$, $In_2O_3$, $SnO_2$, $Na_xPt_3O_4$, conducting polymers metals such as platinum, copper, gold, silver etc., polarize with application of an electric field. In some embodiments, the conductive material is a conducting polymer, or an insulating polymer with conductive fillers. Suitable conductive polymers are disclosed in U.S. Pat. No. 5,571,401, which issued Nov. 5, 1996, and WO 99/31494, which published on Jun. 24, 1999. As disclosed in WO 99/31494, the sensors taught therein comprise substituted polythiophenes. One polymer is poly (3,3"-dihexyl-2-

2":5',2"-terthiophene). In a preferred embodiment, the conductive particle is carbon black.

In an equally preferred embodiment, the conductive material can be a particle, such as a gold nanoparticle, with a capping ligand shell. A preferred nanoparticle is disclosed in WO 99/27357, entitled "Materials, Method and Apparatus for Detection and Monitoring Chemical Species," published Jun. 3, 1999. Examples of colloidal nanoparticles for use in accordance with the present invention are described in the literature (see, Templeton et al. J. Am. Chem. Soc. (1998) 120:1906-1911; Lee et al., Isr. J. Chem. (1997) 37:213-223 (1997); Hostetler et al. LANGMUIR (1998) 14:17-30; Ingram et al., J. Am. Chem. Soc., (1997) 119:9175-9178; Hostetler et al., J. Am Chem. Soc. (1996) 118:4212-4213; Henglein J. Phys. Chem. (1993) 97:5457-5471; Zeiri, J. Phys. Chem. (1992) 96:5908-5917; Leff et al., LANGMUIR (1996) 4723-4730. Moreover, particles such as copper phthalocyanine and phenothiazine polarize when illuminated. All of these polarization techniques can be used to generate sensors of the present invention.

Polarization processing, such as magnetic field processing, involves exposure to various polarization mechanisms having different directions and optionally, different strengths. For example, during fabrication of the present sensors, exposure to a magnetic field can optionally be in one direction, such as in the x-, y- or z-direction; in two directions, such as x- and y-directions, x-and z-directions or y- and z-directions; or in three directions, such as x-, y- and z-directions. In a preferred embodiment, the polarization processing is along the same axis as the vapor measurement. For instance, if the vapor measurement is along the z-direction, particle alignment will be along the z-direction. In an equally preferred embodiment, the direction of expansion of the alternating regions is along the same axis as the vapor measurement. As used herein, the x-, y-, and z-axes have their traditional meaning, i.e., the x and y axes are in the plane of the sensor substrate and the z axis is perpendicular to the x and y origins.

In addition to magnetic field processing, sensor fabrication of the present invention can include other modes of polarization. For example, photosensitive conductive material will be exposed to optical radiation, such as visible, infrared or ultraviolet light. Electrosensitive conductive material involves exposure to electric fields having different directions and different strengths.

As previously discussed, enhancing the response of the sensor can be accomplished by confining the direction of expansion of the alternating regions to be along the axis of measurement or, preferably, along the axis of the particle alignment. For instance, a polymer can have a 2% volume expansion on exposure to a certain vapor concentration. If this swelling can be isolated to one dimension, then the linear expansion can be as high as 8% causing a much larger change in resistance than would occur without confinement.

Aligning the conductive region e.g., material or particles, in a nonconducting matrix during deposition causes an increase in the number of conductive paths which in turn, results in a very low base resistance. As discussed earlier, the formation of a conductive path is related to the percolation threshold of the material. The percolation threshold varies from material to material depending on factors, such as particle size, shape and composition. Alignment of the conductive region will cause percolation to occur at a much lower volume loading. Thus, sensors containing aligned conductive regions will give a larger signal when exposed to a vapor compared to a sensor without aligned regions. As the nonconductive region, such as an organic polymer, swells, disruption of the particle chains occurs and a lowering in the conductivity or an increase in the resistance occurs. As the polymer desorbs, the particles return to their minimum energy state that corresponds to particle alignment.

Non-sensor alignment of particles are known. For instance, U.S. Pat. No. 4,177,228 issued to Prolss, entitled "Method of Production of a Micro-Porous Membrane for Filtration Plants," discloses the alignment of particles by various techniques. Likewise, U.S. Pat. No. 5,742,223, issued to Simenddinger, entitled "Laminar Non-linear Device with Magnetically Aligned Particles," discloses composites with magnetically and electrically conductive particles. In addition, U.S. Pat. No. 4,838,347, issued to Dentini, entitled "Thermal Conductor Assembly," discloses a polymer field with thermally conducting magnetically aligned particles. Furthermore, U.S. Pat. No. 5,104,210, issued to Tokas, entitled "Light Control Films and Method of Making," discloses composites of magnetically alignable particles.

In certain aspects, the present invention relates to conductive regions capable of alignment including, but not limited to, conductive, semi-conductive, magnetic and photoresponsive particles embedded in a nonconductive region, such as an organic matrix. For instance, in one embodiment, particles suitable for use, while preferably spherical, are not limited by their shape and can even be in the form of flakes. Suitable particulate materials that are magnetic include, but are not limited to, metals such as, nickel, cobalt and iron and their magnetic alloys. Other suitable magnetic particles include, but are not limited to, oxides and intermetallic compounds as are known in the art. Composite materials can also be used. These material include, but are not limited to, nickel coated with copper, or magnetically thermally conducting ceramics (see, U.S. Pat. No. 4,838,347, incorporated herein by reference). Additional magnetic particles include, but are not limited to, alloys containing nickel, iron, cobalt and ferrites. Also conductive surface coatings can be used. Precious metal coatings include, but are not limited to, silver, gold and precious metal alloys (see, U.S. Pat. Nos. 4,923,739 and 4,737,112 incorporated herein by reference).

In certain embodiments, the conductive region can be a substrate, such as a particle, coated with metal. Suitable substrates include, but are not limited to, glass, silicon, quartz, ceramic or combination thereof.

The present invention has advantages over current sensor technology. One advantage is the use of lower concentrations of particles, which leads to ease of dispersion. To a first approximation, the rate of particle sedimentation is proportional to the number of particles in the dispersion. Another advantage is the increased stability of the sensors of the present invention, especially when the polymer matrix is crosslinked (i.e., the polymer molecules are interconnected forming a 3-dimensional network). A third advantage is an increase in the sensitivity of the sensors leading to lower limits of detection (i.e., increased dynamic range). The latter advantage is due to the much higher signal-to-noise ratio given by the sensors having an aligned conductive region.

More particularly, the major advantage of this invention over the sensors of the prior art is that the signal-to-noise ratio is much higher. Because of the increase in the signal-to-noise ratio, the limit of detection increases (i.e., a smaller concentration of analyte is capable of detection). In addition, the response time is faster. A faster response time is critical in applications such as quality control where the analyte may be on a conveyor belt with a very short time for detection. In general, sensors with greater response times are better than sensor with lower response times. Various sensor responses of the present invention include, but are not limited to, resistance, capacitance, inductance, impedance, and combinations thereof.

In certain aspects, the nonconductive region of the sensors comprise an organic material. In certain preferred aspects, the organic material is an organic polymer. Organic polymers suitable for use in the present invention include, but are not limited to, those set forth in Table 1.

TABLE I

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), etc. |
| Main-chain acyclic heteroatom polymers | poly(oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), etc. |
| Main-chainheterocyclic polymers | poly(furan tetracarboxylic acid diimides), poly(benzoxazoles), poly(oxadiazoles), poly(benzothiazinophenothiazines), poly(benzothiazoles), poly(pyrazinoquinoxalines), poly(pyromellitimides), poly(quinoxalines), poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), carbohydrates, etc. |

The sensors of the present invention can be fabricated by many techniques including, but not limited to, solution casting, suspension casting, matrix assisted pulsed laser evaporation (MAPLE), MAPLE-Direct Write (MAPLE-DW) (see, R. Andrew McGill, et al., IEEE Transactions on Ultrasonics, Ferroelectrics, and Frequency Control 45:1370-1380 (1998), and mechanical mixing. In general, solution casting routes are advantageous because they provide homogeneous structures and are easy to process. With solution casting routes, resistor elements can be easily fabricated by spin, spray or dip coating. Since all elements of the resistor must be soluble, solution casting routes can be somewhat limited in their applicability. Suspension casting still provides the possibility of spin, spray or dip coating, but more heterogeneous structures than with solution casting are expected. With mechanical mixing, there are no solubility restrictions since it involves only the physical mixing of the resistor components, but device fabrication is more difficult since spin, spray and dip coating are no longer possible. In certain embodiments, the resistor is deposited as a surface layer on a solid matrix that provides means for supporting the leads. Typically, the solid matrix is a chemically inert, nonconductive substrate, such as a glass or ceramic.

Sensor arrays of the present invention are particularly well-suited to scaled up production by being fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip that contains the circuitry for analogue signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case, rather than multiple colors, a plurality of different polymers in a solution which can be deposited are used. A sensor array of a million distinct elements only requires a 1 cm×1 cm sized chip employing lithography at the 10 µm feature level, which is within the capacity of conventional commercial processing and deposition methods. This technology permits the production of sensitive, small-sized, stand-alone chemical sensors.

The fabrication of the sensors of the present invention involves polarization processing of the conductive material. Suitable polarization processing includes, but is not limited to, magnetic field processing which involves exposure to magnetic fields, photolytic field processing which involves exposure to optical radiation, electric field processing which involves exposure to electric fields, and combinations thereof. In photolytic field processing, light sensitive material can be exposed to optical radiation, such as visible, infrared, or ultraviolet light (see, U.S. Pat. No. 4,737,112). All of the foregoing polarization processing techniques can have different axes direction and different strengths.

Preferred sensor arrays have a predetermined inter-sensor variation in the structure or composition of the nonconductive regions (e.g., the nonconductive organic material). The variation can be quantitative and/or qualitative. For example, the concentration of the nonconductive organic material in the blend can be varied across sensors. Alternatively, a variety of different alignment techniques are possible within the sensor array. For example, the polarization processing techniques (e.g., magnetic and electric fields) can vary across the array of sensors.

An electronic nose for detecting an analyte in a fluid is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis.

As such, in another embodiment, the present invention, relates to a system for detecting an analyte in a fluid, comprising: a sensor array comprising first and second sensors wherein the first sensor comprises a region of aligned conducting material. Preferably, the first and second sensors are first and second chemically sensitive resistors, each chemically sensitive resistor comprising a plurality of alternating regions comprising a nonconductive region, such as a nonconductive organic material, and an aligned conductive region, such as an aligned conductive material compositionally different than the nonconductive region. Each resistor provides an electrical path through the alternating nonconducting region and the aligned conductive regions, a first response such as an electrical resistance, when contacted with a first fluid comprising an analyte at a first concentration and a second different response when contacted with a second fluid comprising the analyte at a second different concentration, the difference between the first response and the second response of the first sensor being different from the difference between the first response and the second response of the second sensor under the same conditions; an electrical measuring device electrically connected to the sensor array; and a computer comprising a resident algorithm; the electrical measuring device detecting the first and said second responses in each of the sensors and the computer assembling the responses into a sensor array response profile.

Typically, such sensor arrays and electronic noses of the present invention comprise at least ten, usually at least 100, and often at least 1000 different sensors, though with mass deposition fabrication techniques described herein or otherwise known in the art, arrays of on the order of at least $10^6$ sensors are readily produced.

In operation, preferably each resistor provides a first electrical resistance between its conductive leads when the resistor is contacted with a first fluid comprising an analyte at a first concentration, and a second electrical resistance between its conductive leads when the resistor is contacted with a second fluid comprising the same analyte at a second different concentration. The fluids can be liquid or gaseous in nature. The first and second fluids may reflect samples from two different environments, a change in the concentration of an analyte in a fluid sampled at two time points, a sample and a negative control, etc. The sensor array necessarily comprises sensors that respond differently to a change in an analyte concentration, i. e., the difference between the first and second electrical resistance of one sensor is different from the difference between the first and second electrical resistance of another sensor. In addition, the sensor array can comprise redundant sensors that can be advantageous for maximizing the signal and thus reducing the noise in the signal.

Figure 4:
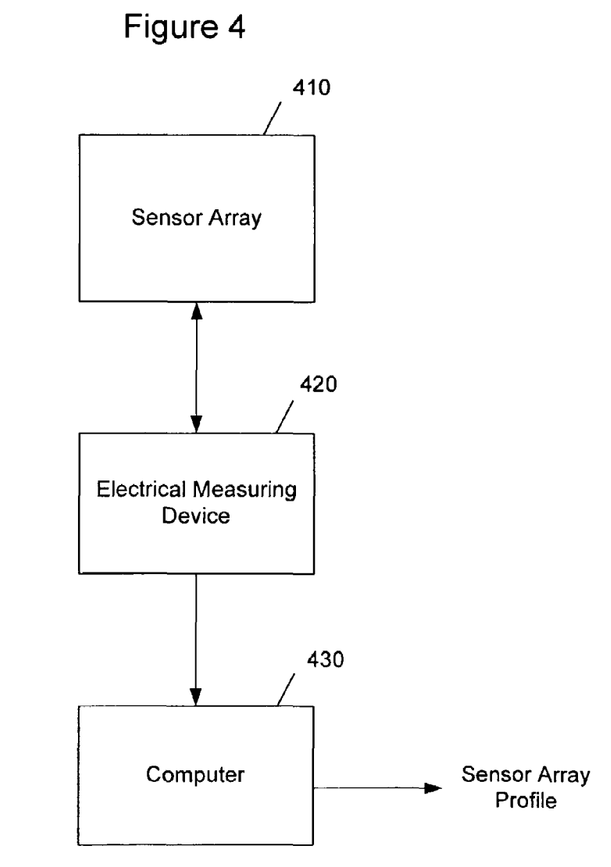
FIG. 4 shows a system for detecting an analyte according to a preferred embodiment of the invention.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analyses, a structure-function database correlating analyses and response profiles is generated. Unknown analyte can then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. FIG. 4 shows a sensor array 410, an electrical measuring device 420, and a computer 430, according to the preferred embodiments. The electrical measuring device 420 measures electrical characteristics of the sensor array 410, and provides the information to the computer 430, which outputs a sensor array response profile. In another embodiment, the electrical measuring device is an integrated circuit comprising neural network-based hardware and a digital-analog converter (DAC) multiplexed to each sensor, or a plurality of DACs, each connected to different sensor(s).

A wide variety of analytes and fluids may be analyzed by the disclosed sensors, arrays and noses so long as the subject analyte is capable of generating a differential response across a plurality of sensors of the array. Analyte applications include broad ranges of chemical classes including, but not limited to, organics such as alkanes, alkenes, alkynes, dienes, alicyclic hydrocarbons, arenes, heterocyclics, alcohols, ethers, ketones, aldehydes, carbonyls, carbanions, polynuclear aromatics and derivatives of such organics, e.g., halide derivatives, etc., microorganism off-gases, fungi, bacteria, microbes, viruses, metabolites, biomolecules such as sugars, isoprenes and isoprenoids, fatty acids and derivatives, etc.

Accordingly, commercial applications of the sensors, arrays and noses include environmental toxicology and remediation, biomedicine, materials quality control, food and agricultural products monitoring. Further applications include, but are not limited to: heavy industrial manufacturing (automotive, aircraft, etc.), such as ambient air monitoring, worker protection, emissions control, and product quality testing; oil/gas petrochemical applications, such as combustible gas detection, $H_2S$ monitoring, and hazardous leak detection and identification; emergency response and law enforcement applications, such as illegal substance detection and identification, arson investigation, hazardous spill identification, enclosed space surveying, and explosives detection; utility and power applications, such as emissions monitoring and transformer fault detection; food/beverage/agriculture applications, such as freshness detection, fruit ripening control, fermentation process monitoring and control, flavor composition and identification, product quality and identification, and refrigerant and fumigant detection; cosmetic/perfume applications, such as fragrance formulation, product quality testing, and patent protection fingerprinting; chemical/plastics/pharmaceuticals applications, such as fugitive emission identification, leak detection, solvent recovery effectiveness, perimeter monitoring, and product quality testing; hazardous waste site applications, such as fugitive emission detection and identification, leak detection and identification, and perimeter monitoring; transportation applications, such as hazardous spill monitoring, refueling operations, shipping container inspection, and diesel/gasoline/aviation fuel identification; building/residential applications, such as natural gas detection, formaldehyde detection, smoke detection, automatic ventilation control (cooking, smoking, etc.), and air intake monitoring; hospital/medical applications, such as anesthesia and sterilization gas detection, infectious disease detection, breath, wound and body fluids analysis, and telesurgey.

In yet another aspect, the present invention relates to a method for detecting the presence of an analyte in a fluid comprising: providing a sensor array comprising first and second sensors, wherein the first sensor comprises a region of aligned conductive material; and contacting the sensor array with the analyte to produce a response thereby detecting the presence of the analyte. Preferably, the first and second sensors are first and second chemically sensitive resistors each comprising a plurality of alternating nonconductive regions, such as nonconductive organic material, and aligned conductive regions, such as an aligned conductive material compositionally different than the nonconductive region, each resistor providing an electrical path through the nonconducting region and aligned conductive region, a first response such as an electrical resistance, when contacted with a first fluid comprising an analyte at a first concentration and a second different response when contacted with a second fluid comprising the analyte at a second different concentration.

The general method for using the disclosed sensor arrays and electronic noses for detecting the presence of an analyte in a fluid preferably involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration.

In certain embodiments, the methods and systems of the present invention can be used for monitoring medical conditions and disease processes. For instance, WO 98/29563, published Jul. 9, 1998, and incorporated herein by reference, discloses a method for monitoring conditions in a patient wherein a sample is obtained from a patient over a period of time. The samples are then flowed over a gas sensor and a response is measured. Thereafter, the response is correlated with known responses for known conditions. The conditions include, but are not limited to, the progression and or regression of a disease state, bacterial infections, viral, fungal or parasitic infections, the effectiveness of a course of treatment and the progress of a healing process.

In another embodiment, the methods and systems of the present invention can be used for monitoring medical conditions in a respiring subject. For instance, WO 98/39470, published Sep. 11, 1998, and incorporated herein by reference, discloses a method for detecting the occurrence of a condition in a respiring subject. The method comprises introducing emitted respiratory gases to a gas sensing device, detecting certain species present in the gas and correlating the presence of the species with certain conditions. A wide variety of conditions can be ascertained using this aspect of the present invention. These conditions include, but are not limited to, halitosis, ketosis, yeast infections, gastrointestinal infections, diabetes, alcohol, phenylketonuria, pneumonia, and lung infections. Those of skill in the art will know of other conditions and diseases amenable to the methods and systems of the present invention.

In certain aspects, the sensor arrays, systems and methods of the present invention comprise: first and second sensors wherein the first sensor comprises a region of aligned conducting material. The second sensor can also comprise a region of aligned conductive material. However, in certain other embodiments, the second sensor is a different sensor type. Suitable sensor types include, but are not limited to, a surface acoustic wave (SAW) sensor; a quartz microbalance sensor; a conductive composite; a metal oxide gas sensor, an organic gas sensor; an infrared sensor; a sintered metal oxide sensor; a phthalocyanine sensor; an electrochemical cell; a conducting polymer sensor; a catalytic gas sensor; an organic semiconducting gas sensor; a solid electrolyte gas sensor; a temperature sensor; a humidity sensor; fiber optic micromirrors; dye impregnated polymeric coatings on optical fibers and a Langmuir-Blodgett film sensor. Those of skill in the art will know of other sensors suitable for use in the present invention.

In certain aspects, the sensors of the present invention comprise a chiral center. For instance, European Patent Application No. 0 794 428, published Sep. 10, 1997, describes sensors capable of distinguishing between enantiomers. The sensor comprise a pair of spaced apart contacts and a conducting polymer material spanning the gap. The polymer has chiral sites in the polymer material formed by incorporating optically active counter ions such as camphor sulfonic acid.

Moreover, WO 99/40423, published Aug. 12, 1999, discloses sensor arrays of that are capable of distinguishing or differentiating between chiral compounds. That publication relates to a device for detecting the presence or absence of an analyte in a fluid, the device comprises a sensor, the sensor comprising a chiral region. The sensor comprises a conductive region and a nonconductive region, wherein at least one of the conductive and nonconductive regions is chiral, and wherein the analyte generates a differential response across the sensor.

In certain other embodiments, the sensor arrays of the present invention comprise sensors disclosed in WO 99/00663, published Jan. 7, 1999. As taught therein, a combinatorial approach for preparing arrays of chemically sensitive polymer-based sensors are capable of detecting the presence of a chemical analyte in a fluid contact therewith. The described methods and devices comprise combining varying ratios of at least first and second organic materials which, when combined, form a polymer or polymer blend that is capable of absorbing a chemical analyte, thereby providing a detectable response. The detectable response of the sensors prepared by this method is not linearly related to the mole fraction of at least one of the polymer-based components of the sensor.

The following examples are offered by way of illustration and not by way of limitation.

EXAMPLES

Example 1

This Example illustrates the difference in percolation threshold in non-aligned sensors versus aligned sensors.

Figure 1:
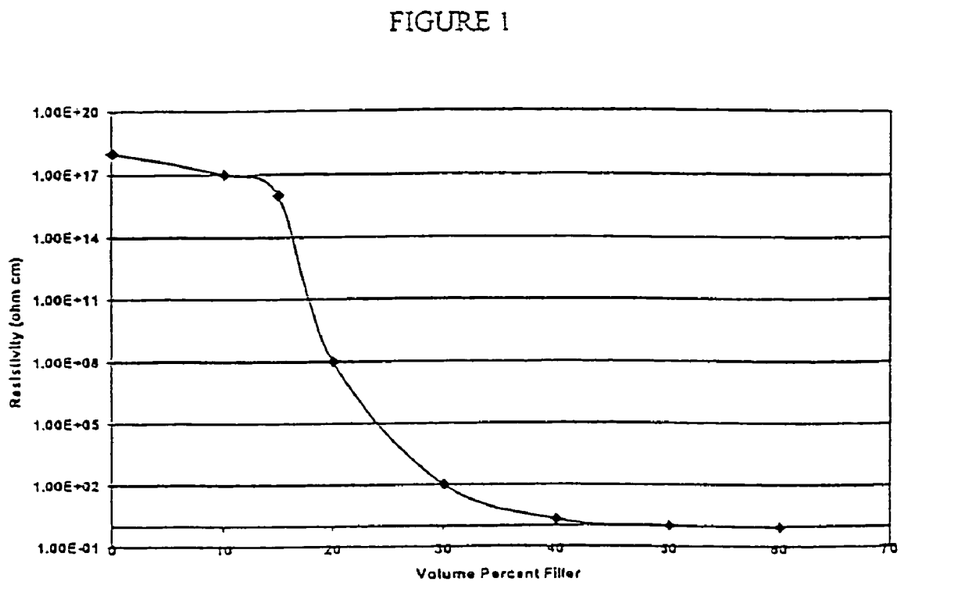
FIG. 1 shows a graph of a typical resistance versus volume loading for a non-aligned composite sensor.
Figure 2:
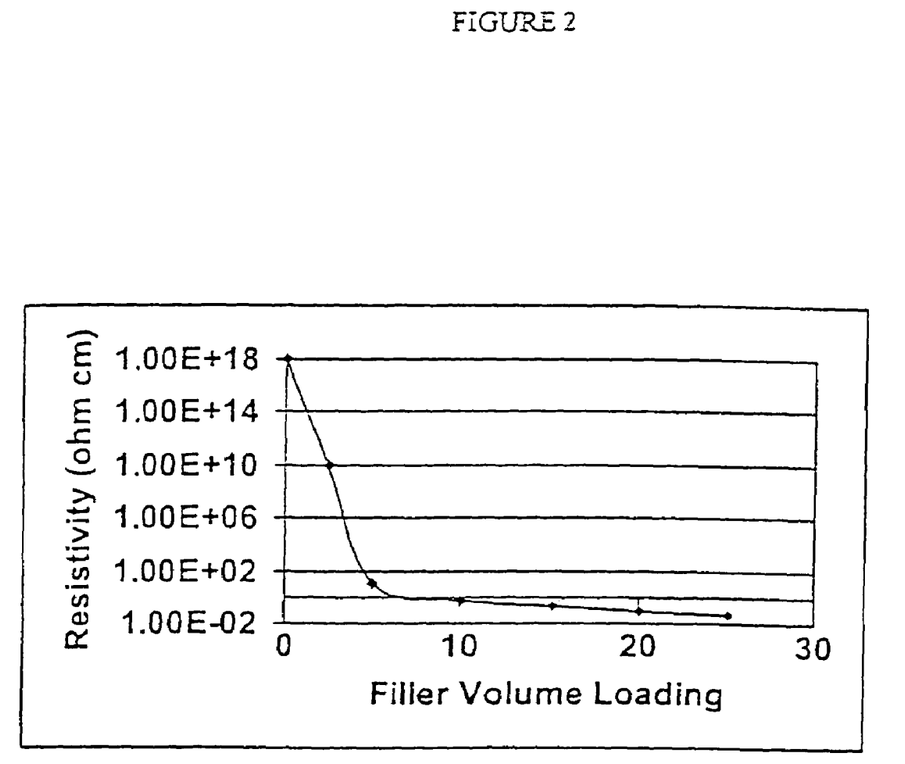
FIG. 2 shows a graph of resistance versus volume loading for a composite sensor where the particles have been aligned.

The percolation threshold is defined as the particle volume fraction at which the conductivity of the resistor increases rapidly i.e., an infinite number of conductive paths are formed and the lattice essentially transforms from an insulator to a conductor. FIG. 1 illustrates a typical resistance versus volume loading for a non-aligned composite sensor, where the percolation threshold occurs at about 20 volume percent filler. FIG. 2 shows a graph of resistance versus volume loading for a composite sensor where the particles have been aligned. The percolation threshold occurs at about 5 volume percent filler.

Example 2

This Example illustrates a sensor array that was fabricated by depositing Black Pearl 2000 (40 wt %) dispersed in 1,2-polybutadiene in the presence of an electric field.

Figure 3:
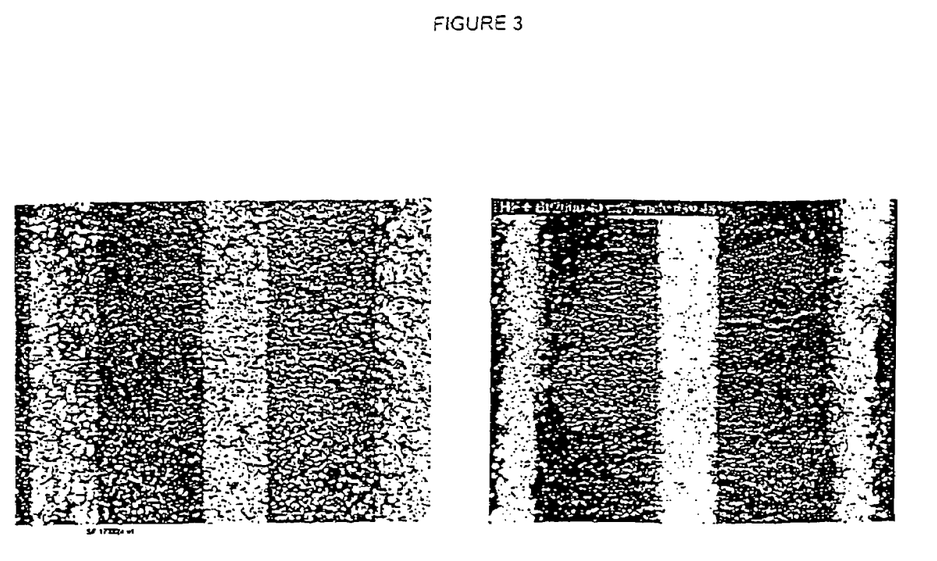
FIG. 3 shows optical micrographs of unaligned sensor (left) and aligned sensor (right) Black Pearl 2000 (40 wt %) in 1,2-polybutadiene.

The conductive particles respond to the field by migrating to minimum energy states, which in this case corresponds to chain-like structures aligned parallel to the electric field. As the solvent evaporates the chains are locked in place. FIG. 3 illustrates the particle alignment after using 48 volts across the sensor electrodes during the deposition process.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A system for detecting an analyte in a fluid, said system comprising:

a sensor array comprising first and second sensors wherein said first sensor comprises a region of aligned conductive material which provides a response in the presence of said analyte;

an electrical measuring device electrically connected to the sensor array; and a computer comprising a resident algorithm; the electrical measuring device detecting the response and the computer assembling the response into a sensor array response profile, wherein said first and said second sensors are first and second chemically sensitive resistors, each chemically sensitive resistor comprising a plurality of alternating regions comprising a nonconductive region and an aligned conductive region that is compositionally different than said nonconductive region wherein, each resistor provides an electrical path through said nonconductive region and said aligned conductive region, a first electrical resistance when contacted with a first fluid comprising an analyte at a first concentration and a second different electrical resistance when contacted with a second fluid comprising said analyte at a second different concentration wherein, the difference between said first electrical resistance and said second electrical resistance of said first chemically sensitive resistor being different from the difference between said first electrical resistance and said second electrical resistance of said second chemically sensitive resistor under the same conditions; and the electrical measuring device detecting the first and said second electrical resistances in each of said chemically sensitive resistors and the computer assembling the resistances into a sensor array response profile.

2. The system for detecting an analyte in a fluid in accordance with claim 1, wherein said conductive region is aligned by exposure to a member selected from the group consisting of an electric field, a thermal field, a magnetic field, an electromagnetic field, a photoelectric field, a light field and combinations thereof.

3. The system for detecting an analyte in a fluid in accordance with claim 2, wherein said conductive region is electrically aligned.

4. The system for detecting an analyte in a fluid in accordance with claim 2, wherein said conductive region is magnetically aligned.

5. The system array for detecting an analyte in a fluid in accordance with claim 2, wherein said conductive region is photolytically aligned.

6. A system for detecting an analyte in a fluid said system comprising:

a sensor array comprising first and second sensors wherein said first sensor comprises a region of aligned conductive material which provides a response in the presence of said analyte;

an electrical measuring device electrically connected to the sensor array; and a computer comprising a resident algorithm; the electrical measuring device detecting the response and the computer assembling the response into a sensor array response profile.

wherein the first sensor and the second sensor each comprises regions of nonconductive materials, and wherein the respective regions of nonconductive materials of the first and second sensors have a different concentration of a same type of nonconductive organic material with respect to each other.

7. A system for detecting an analyte in a fluid said system comprising:

a sensor array comprising first and second sensors wherein said first sensor comprises a region of aligned conductive material which provides a response in the presence of said analyte:

an electrical measuring device electrically connected to the sensor array:

a computer comprising a resident algorithm; the electrical measuring device detecting the response and the computer assembling the response into a sensor array response profile, and aligning means for alignment the region of aligned conductive material, wherein the region of aligned conductive material is aligned by the aligning means by exposure to a plurality of different polarization mechanisms having different directions and different strengths.

8. A system for detecting an analyte in a fluid said system comprising:

a sensor array comprising first and second sensors wherein said first sensor comprises a region of aligned conductive material which provides a response in the presence of said analyte;

an electrical measuring device electrically connected to the sensor array;

a computer comprising a resident algorithm; the electrical measuring device detecting the response and the computer assembling the response into a sensor array response profile, and aligning means for alignment the region of aligned conductive material, wherein the region of aligned conductive material is aligned by the aligning means by exposure to a plurality of different polarization mechanisms having different strengths with respect to each other.

* * * * *